US012325864B2

(12) United States Patent
Thompson

(10) Patent No.: US 12,325,864 B2
(45) **Date of Patent: *Jun. 10, 2025**

(54) RECOMBINANT VIRUS VECTOR (RVV) FOR INHIBITING EPIDERMAL GROWTH FACTOR RECEPTOR (EGFR) ACTIVITY AND METHOD OF MAKING AN AGENT/TARGET CELL COMPLEX TO INCREASE CETUXIMAB-LIKE PROTEIN (CLP) PRODUCTION

(71) Applicant: Kinase Pharma Inc., Calgary (CA)

(72) Inventor: Bradley G. Thompson, Calgary (CA)

(73) Assignee: Kinase Pharma Inc., Calgary (CA)

( * ) Notice: Subject to any disclaimer, the term of this patent is extended or adjusted under 35 U.S.C. 154(b) by 18 days.

This patent is subject to a terminal disclaimer.

(21) Appl. No.: 18/158,852

(22) Filed: Jan. 24, 2023

(65) Prior Publication Data

US 2023/0340533 A1 Oct. 26, 2023

Related U.S. Application Data

(63) Continuation of application No. 17/313,801, filed on May 6, 2021, now Pat. No. 11,603,541.

(51) Int. Cl.

| | |
|---|---|
| ***C12N 15/86*** | (2006.01) |
| ***A61K 48/00*** | (2006.01) |
| ***C07K 16/28*** | (2006.01) |

(52) U.S. Cl.

CPC .......... *C12N 15/86* (2013.01); *C07K 16/2863* (2013.01); *A61K 48/00* (2013.01); *C07K 2317/24* (2013.01); *C12N 2330/50* (2013.01); *C12N 2750/14143* (2013.01)

(58) Field of Classification Search

CPC ...................... C12N 15/86; C12N 2750/14143

See application file for complete search history.

(56) References Cited

U.S. PATENT DOCUMENTS

| | | | | |
|---|---|---|---|---|
| 6,764,845 | B2 * | 7/2004 | Sista | A61K 9/0019 435/235.1 |
| 8,367,069 | B2 | 2/2013 | Ferris | |
| 9,163,259 | B2 * | 10/2015 | Choi | A61P 27/02 |
| 10,494,645 | B2 | 12/2019 | Auricchio et al. | |

OTHER PUBLICATIONS

Xing M, et al. (Apr. 5, 2016) Oncotarget. 7(19):28262-28272.*

Yan Z, et al. (Jan. 2005) Journal of Virology. 79(1):364-379. (doi:10.1128/JVI.79.1.364-379.2005).*

Paul, WE (1993) Fundamental Immunology, 3rd ed. Raven Press, NY, Chap. 9, pp. 292-295.*

Rudikoff, S et al. (1982) Proc. Natl. Acad. Sci. USA, 79:1979-1983 (doi: 10.1073/pnas.79.6.1979).*

Colman, PM (1994) Research in Immunology, Elsevier, NY, 145(1):33-36.*

Bendig M. M. (1995) Methods: A Companion to Methods in Enzymology, 8:83-93.*

MacCallum et al. (Oct. 11, 1996) J. Mol. Biol., 262(5):732-745. (doi: 10.1006/jmbi.1996.0548).*

Casset et al (2003) Biochemical and Biophysical Research Communications, 307:198-205. (doi:10.1016/S0006-291X(03)01131-8).*

Chen et al. (1995) EMBO J., 14(12):2784-2794. (doi: 10.1002/j.1460-2075.1995.tb07278.x).*

Wang D, et al. (May 2018). Nature Reviews Drug Discovery 18:358-378. (https://doi.org/10.1038/s41573-019-0012-9).

Wilmott P, et al. (2019). Human Gene Therapy Methods 30(6):206-213. (DOI: 10.1089/hgtb.2019.276).

* cited by examiner

*Primary Examiner* — Robert S Landsman

(74) *Attorney, Agent, or Firm* — Gowling WLG (Canada) LLP

(57) ABSTRACT

The present disclosure relates to one or more agents, therapies, treatments, and methods of use of the agents and/or therapies and/or treatments for increasing production of a Cetuximab-like protein (CLP) by a subject that is administered the agent, therapy or treatment. Embodiments of the present disclosure can be used as a therapy or a treatment for a subject that has a condition that may benefit from reducing the DNA synthesis of genes that regulate cellular growth and proliferation.

5 Claims, 1 Drawing Sheet

Specification includes a Sequence Listing.

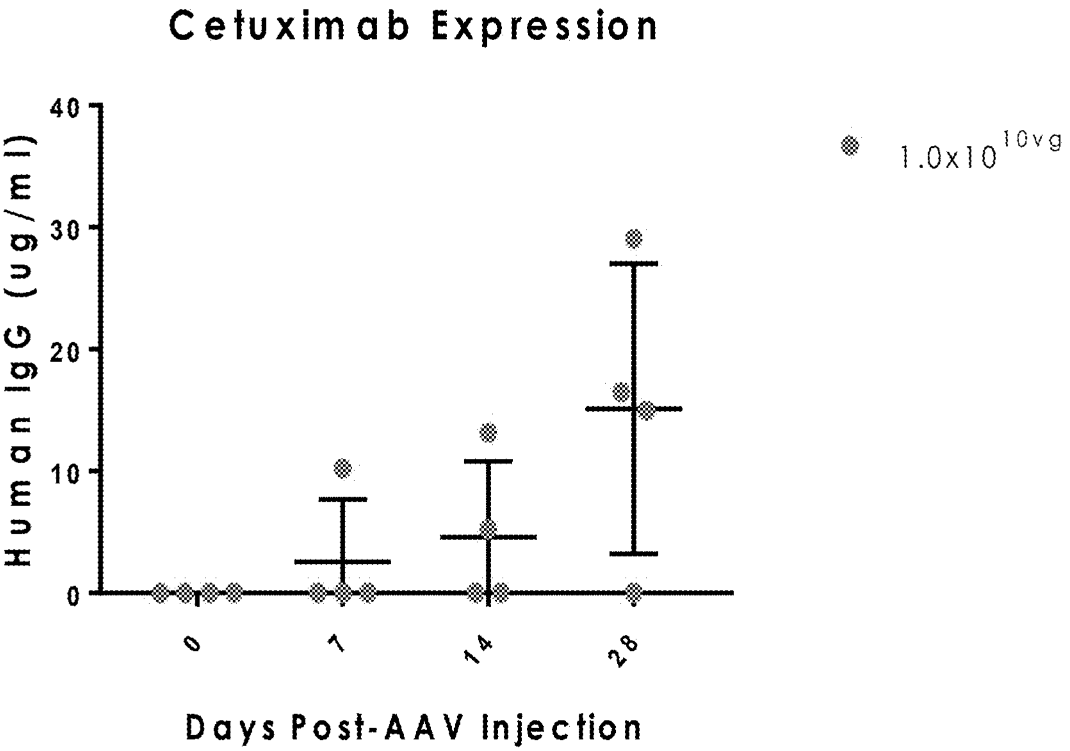
Cetuximab Expression
Human IgG (ug/ml)
40
30
20
10
0
0
7
14
28
Days Post-AAV Injection
1.0x10^10vg

RECOMBINANT VIRUS VECTOR (RVV) FOR INHIBITING EPIDERMAL GROWTH FACTOR RECEPTOR (EGFR) ACTIVITY AND METHOD OF MAKING AN AGENT/TARGET CELL COMPLEX TO INCREASE CETUXIMAB-LIKE PROTEIN (CLP) PRODUCTION

SEQUENCE LISTING

This application contains a Sequence Listing electronically submitted via Patent Center to the United States Patent and Trademark Office as an XML Document file entitled "A8145603USCON-ST26.xml" created on Jun. 1, 2023 and having a size of 24,288 bytes. The information contained in the Sequence Listing is incorporated by reference herein.

TECHNICAL FIELD

The present disclosure generally relates to compositions and methods for regulating tumor cell growth. In particular, the present disclosure relates to compositions and methods for regulating endogenous production of an inhibitor of growth factors that facilitate cancer cell DNA synthesis and cancer cell growth.

BACKGROUND

Epidermal Growth Factor Receptor (EGFR) is a cell surface receptor that spans the cell membrane with an extracellular ligand-binding domain and an intracellular signaling domain. Upon a binding event with a ligand, such as epidermal growth factor and transforming growth factor alpha, EGFR transitions to an active state. In the active state, the EGFR may undergo a dimerization event, which then activates the intracellular signaling domain. In particular, the activated intracellular signaling domain activates a protein-tyrosine kinase enzyme, which activates one or more intracellular cell signaling pathways to ultimately activate synthesis of deoxyribonucleic acid (DNA) synthesis and, in particular, genes associated with cell growth and proliferation.

It is known that dysregulation of EGFR, such as through mutant EGFR phenotypes or otherwise, can result in overstimulation, also referred to as amplification and upregulation, and this overstimulation has been causally linked to various cancers. In effect, the EGFR signaling pathway results in excessive DNA synthesis in tumor cells and, therefore, growth and proliferation of the tumor cells.

In efforts to treat such dysregulated-EGFR related cancers, a number of monoclonal antibody (mAB) protein therapies have been developed. In general, the mAB protein therapies can bind to the extracellular ligand-binding domain inhibit EGFR and that prevents a binding event with any stimulatory ligand, ultimately inhibiting the intracellular signaling and DNA synthesis activation.

Currently, mAB protein therapies require that a patient attend a clinic or hospital setting for intravenous administration. This intravenous administration can be costly, distruptive to the patient's life and potentially expose the patient to a greater risk of acquiring a healthcare-acquired nosocomial infection.

SUMMARY

Some embodiments of the present disclosure relate to compositions and methods that cause a subject to produce a monoclonal antibody (mAB) protein that can act as a targeted therapy for cancer. In some embodiments of the present disclosure, the mAB binds to and inhibits Epidermanl Growth Factor Receptor (EGFR) by binding to the extracellular ligand-binding domain of EGFR. This mAB binding blocks the EGFR's ability to bind other stimulatory ligands and it may reduce excessive deoxyribonucleic acid (DNA) synthesis in tumor cells and, therefore, growth and proliferation of the tumor cells. Some embodiments of the present disclosure relate to compositions and methods that cause a subject to produce a mAB that is substantially similar, or similar or the same as Cetuximab, referred to herein as a Cetuximab-like protein (CLP). In some embodiments of the present disclosure, the subject's production of the CLP is endogenous. The CLP may be bioavailable and functionally equivalent to an exogenously administered Cetuximab.

In some embodiments of the present disclosure, the compositions described herein comprise a vector of plasmid DNA that includes an insert sequence of nucleic acids. The insert sequence encodes for the production of the CLP and the insert sequence may also include a backbone sequence of nucleic acids that facilitates introduction of the insert sequence into one or more of a subject's cells. Within the subject's cells, the insert sequence is expressed and/or replicated. Expression of the insert sequence by one or more cells of the subject results in an increased production of the CLP by the subject. In some embodiments of the present disclosure, the methods that upregulate the production of CLP and to methods of manufacturing and administering the compositions that result in a subject's increased production of CLP.

Some embodiments of the present disclosure relate to compositions and methods that can be used as a therapy or a treatment for a subject that has a condition associated with increased growth and/or proliferation of tumor cells. The embodiments of the present disclosure may result in a subject who receives such therapy or treatment to increase production of the CLP. The CLP may interfere with the biological activity of EGFR. Some embodiments of the present disclosure relate to a recombinant virus vector (RVV) that forms part of such therapy or treatment. The RVV comprises a nucleotide sequence encoding production of the CLP so that a recipient of the RVV may then produce the CLP from their own cells.

Some embodiments of the present disclosure relate to a composition that comprises a nucleotide sequence according to the present disclosure (SEQ ID No. 9) of which at least a portion can be expressed in a target cell.

Some embodiments of the present disclosure relate to an insert for use with an RVV, wherein the insert has a nucleotide sequence has one or more of SEQ ID No. 1, SEQ ID No. 2, SEQ ID No. 3, SEQ ID No. 4, SEQ ID No. 5, SEQ ID No. 6, SEQ ID No. 7, or SEQ ID No. 8.

Some embodiments of the present disclosure relate to the insert with one or more of SEQ ID No. 1, SEQ ID No. 2, SEQ ID No. 3, SEQ ID No. 4, SEQ ID No. 5, SEQ ID No. 6, SEQ ID No. 7, or SEQ ID No. 8 for use with an RVV.

Some embodiments of the present disclosure relate to a method of making an agent/target cell complex, the method comprising a step of administering a therapeutically effective amount of the agent to a subject, wherein the agent/target cell complex increases the subject's production of the CLP.

Some embodiments of the present disclosure relate to a pharmaceutical agent that comprises an agent, a pharmaceutically acceptable carrier and/or an excipient. Administering the pharmaceutical agent to a subject may increase the subject's production of the CLP.

Some embodiments of the present disclosure relate to a method of treating a condition. The method comprises a step of administering to a subject a therapeutically effective amount of an agent that upregulates the subject's production of the CLP and the CLP may ameliorate the condition. In some embodiments of the present disclosure, the condition is cancer.

Some embodiments of the present disclosure relate to a use of an agent for treating a condition, wherein the agent upregulates the subject's production of the CLP and the CLP may ameliorate the condition. In some embodiments of the present disclosure, the condition is cancer.

Embodiments of the present disclosure relate to at least one approach for inducing endogenous production of the CLP. A first approach utilizes one or more gene vectors containing nucleotide sequences for increasing the endogenous production of the CLP. The one or more vectors can be administered to a subject to increase the subject's production of the CLP.

In some embodiments of the present disclosure, following administration of the agent the CLP may be produced within the subject's cells as a precursor CLP protein that can be subjected to one or more post-translational modification processes, which results in subject cells that are producing the precursor CLP protein to produce a final CLP product that is bioavailable and functional. In some embodiments of the present disclosure, the CLP product may be capable of participating in a binding event with a specific family of receptor proteins, such as EGFR. Without being bound by any particular theory, when such a binding event occurs, the CLP product can act to prevent further ligands from binding to and/or activating EGFR.

BRIEF DESCRIPTION OF THE DRAWINGS

These and other features of the present disclosure will become more apparent in the following detailed description in which reference is made to the appended drawings.

FIG. 1 is a scatter plot that shows Human IgG expression, indicative of CLP expression, up to 28 days following administration of a vector, according to embodiments of the present disclosure, in mice.

DETAILED DESCRIPTION

Unless defined otherwise, all technical and scientific terms used herein have the meanings that would be commonly understood by one of skill in the art in the context of the present description. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

As used herein, the singular forms "a", "an", and "the" include plural references unless the context clearly dictates otherwise. For example, reference to "an agent" includes one or more agents and reference to "a subject" or "the subject" includes one or more subjects.

As used herein, the terms "about" or "approximately" refer to within about 25%, preferably within about 20%, preferably within about 15%, preferably within about 10%, preferably within about 5% of a given value or range. It is understood that such a variation is always included in any given value provided herein, whether or not it is specifically referred to.

As used herein, the term "activity" is used interchangeably with the term "functionality" and both terms refer to the physiologic action of biomolecule.

As used herein, the term "agent" refers to a substance that, when administered to a subject, causes one or more chemical reactions and/or one or more physical reactions and/or or one or more physiological reactions and/or one or more immunological reactions in the subject. In some embodiments of the present disclosure, the agent is a plasmid vector, such as a recombinant virus vector (RVV) as described herein.

As used herein, the term "ameliorate" refers to improve and/or to make better and/or to make more satisfactory.

As used herein, the term "biomolecule" refers to a carbohydrate, a protein, an amino acid sequence, a nucleic acid, a lipid, a primary metabolite, a secondary metabolite or another metabolite that is found within a subject. A biomolecule may be endogenous or exogenous to a subject.

As used herein, the term "cell" refers to a single cell as well as a plurality of cells or a population of the same cell type or different cell types. Administering an agent to a cell includes in vivo, in vitro and ex vivo administrations and/or combinations thereof.

As used herein, the term "complex" refers to an association, either direct or indirect, between one or more particles of an agent and one or more target cells. In some embodiments, reference to a complex includes uptake of one or more particles of the agent by the target cell. In other embodiments, reference to a complex may include uptake and expression by the target cell of one or more nucleotide sequences carried by the particles of the agent. This association results in a change in the metabolism of the target cell. As used herein, the phrase "change in metabolism" refers to an increase or a decrease in the one or more target cells' production of deoxyribonucleic acid (DNA), ribonucleic acid (RNA), one or more proteins, and/or any post-translational modifications of one or more proteins.

As used herein, the terms "dysregulation" and "dysregulated" refer to situations or conditions wherein homeostatic control systems have been disturbed and/or compromised so that one or more metabolic, physiologic and/or biochemical systems within a subject operate partially or entirely without said homeostatic control systems.

As used herein, the term "effector molecule" refers to a molecule within a subject that can directly or indirectly regulate the metabolic activity of a target cell by increasing or decreasing the production of DNA, RNA and/or amino-acid sequences and/or by increasing or decreasing any post-translational modifications of one or more proteins.

As used herein, the term "endogenous" refers to the production and/or modification of a molecule that originates within a cell of a subject.

As used herein, the term "excipient" refers to any substance, not itself an agent, which may be used as a component within a pharmaceutical composition or a medicament for administration of a therapeutically effective amount of the agent to a subject. Additionally, or alternatively, an excipient may, either alone or in combination with further chemical components, improve the handling and/or storage properties and/or permit or facilitate formation of a dose unit of the agent. Excipients include, but are not limited to, one or more of: a binder, a disintegrant, a diluent, a buffer, a taste enhancer, a solvent, a thickening agent, a gelling agent, a penetration enhancer, a solubilizing agent, a wetting agent, an antioxidant, a preservative, a surface active agent, a lubricant, an emollient, a substance that is added to mask or counteract a disagreeable odor, fragrance or taste, a substance added to improve appearance or texture of the composition and/or a substance that is used to form the pharmaceutical compositions or medicaments. Any such excipients can be used in any dosage forms according to the present disclosure. The foregoing classes of excipients are not meant to be exhaustive but are provided merely to be illustrative of what a person of skill in the art would know and would also recognize that additional types and combinations of excipients may be used to achieve delivery of a therapeutically effective amount of the agent to a subject through one or more routes of administration.

As used herein, the term “exogenous” refers to a molecule that is within a subject but that did not originate within the subject.

As used herein, the terms “inhibit”, “inhibiting”, and “inhibition” refer to a decrease in activity, response, or other biological parameter of a biologic process, disease, disorder or symptom thereof. This can include but is not limited to the complete ablation of the activity, response, condition, or disease. This may also include, for example, a 10% reduction in the activity, response, condition, or disease as compared to the native or control level. Thus, the reduction can be a 10%, 20%, 30%, 40%, 50%, 60%, 70%, 80%, 90%, 100%, or any amount of reduction in between the specifically recited percentages, as compared to native or control levels.

As used herein, the term “medicament” refers to a medicine and/or pharmaceutical composition that comprises the agent and that can promote recovery from a disease, disorder or symptom thereof and/or that can prevent a disease, disorder or symptom thereof and/or that can inhibit the progression of a disease, disorder, or symptom thereof.

As used herein, the term “patient” refers to a subject that is afflicted with a disease or disorder. The term “patient” includes human and veterinary subjects.

As used herein, the term “pharmaceutical composition” means any composition comprising, but not necessarily limited to, an agent to be administered a subject in need of therapy or treatment of a disease, disorder or symptom thereof. Pharmaceutical compositions may include additives such as pharmaceutically acceptable carriers, pharmaceutically accepted salts, excipients and the like. Pharmaceutical compositions may also additionally include one or more further active ingredients such as antimicrobial agents, anti-inflammatory agents, anaesthetics, analgesics, and the like.

As used herein, the term “pharmaceutically acceptable carrier” refers to an essentially chemically inert and non-toxic component within a pharmaceutical composition or medicament that does not inhibit the effectiveness and/or safety of the agent. Some examples of pharmaceutically acceptable carriers and their formulations are described in Remington (1995, The Science and Practice of Pharmacy (19th ed.) ed. A. R. Gennaro, Mack Publishing Company, Easton, PA), the disclosure of which is incorporated herein by reference. Typically, an appropriate amount of a pharmaceutically acceptable carrier is used in the formulation to render said formulation isotonic. Examples of suitable pharmaceutically acceptable carriers include, but are not limited to: saline solutions, glycerol solutions, ethanol, N-(1(2,3-dioleyloxy)propyl)-N,N,N-trimethylammonium chloride (DOTMA), dioleolphosphotidylethanolamine (DOPE), and liposomes. Such pharmaceutical compositions contain a therapeutically effective amount of the agent, together with a suitable amount of one or more pharmaceutically acceptable carriers and/or excipients so as to provide a form suitable for proper administration to the subject. The formulation should suit the route of administration. For example, oral administration may require enteric coatings to protect the agent from degrading within portions of the subject’s gastrointestinal tract. In another example, injectable routes of administration may be administered in a liposomal formulation to facilitate transport throughout a subject’s vascular system and to facilitate delivery across cell membranes of targeted intracellular sites.

As used herein, the phrases “prevention of” and “preventing” refer to avoiding the onset or progression of a disease, disorder, or a symptom thereof.

As used herein, the terms “production”, “producing” and “produce” refer to the synthesis and/or replication of DNA, the transcription of one or more sequences of RNA, the translation of one or more amino acid sequences, the post-translational modifications of an amino-acid sequence, and/or the production of one or more regulatory molecules that can influence the production and/or functionality of an effector molecule or an effector cell. For clarity, “production” is also be used herein to refer to the functionality of a regulatory molecule, unless the context reasonably indicates otherwise.

As used herein, the terms “promote”, “promotion”, and “promoting” refer to an increase in an activity, response, condition, disease process, or other biological parameter. This can include, but is not limited to, the initiation of the activity, response, condition, or disease process. This may also include, for example, a 10% increase in the activity, response, condition, or disease as compared to the native or control level. Thus, the increase in an activity, response, condition, disease, or other biological parameter can be 10%, 20%, 30%, 40%, 50%, 60%, 70%, 80%, 90%, 100%, or more, including any amount of increase in between the specifically recited percentages, as compared to native or control levels.

As used herein, the term “prophylactic administration” refers to the administration of any composition to a subject, in the absence of any symptom or indication of a disease or disorder, to prevent the occurrence and/or progression of the disease or disorder within the subject.

As used herein, the terms “signal molecule”, “signalling molecule” and “regulatory molecule” can be used interchangeably and refer to a molecule that can directly or indirectly affect the production and/or functionality of an effector molecule or effector cell. Signal molecules can be enzymes or other types of biomolecules that can act as a direct ligand on a target cell or they may influence the levels or functionality of a downstream ligand or a receptor for a ligand.

As used herein, the term “subject” refers to any therapeutic target that receives the agent. The subject can be a vertebrate, for example, a mammal including a human. The term “subject” does not denote a particular age or sex. The term “subject” also refers to one or more cells of an organism, an in vitro culture of one or more tissue types, an in vitro culture of one or more cell types, ex vivo preparations, and/or a sample of biological materials such as tissue and/or biological fluids.

As used herein, the term “target cell” refers to one or more cells and/or cell types that are deleteriously affected, either directly or indirectly, by a dysregulated immune system and/or a disease process. The term “target cell” also refers to cells that are not deleteriously affected but that are cells in which it is desired that the agent interacts.

As used herein, the term "therapeutically effective amount" refers to the amount of the agent used that is of sufficient quantity to ameliorate, treat and/or inhibit one or more of a disease, disorder or a symptom thereof. The "therapeutically effective amount" will vary depending on the agent used, the route of administration of the agent and the severity of the disease, disorder or symptom thereof. The subject's age, weight and genetic make-up may also influence the amount of the agent that will be a therapeutically effective amount.

As used herein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and, (c) ameliorating the disease.

As used herein, the terms "unit dosage form" and "unit dose" refer to a physically discrete unit that is suitable as a unitary dose for patients. Each unit contains a predetermined quantity of the agent and optionally, one or more suitable pharmaceutically acceptable carriers, one or more excipients, one or more additional active ingredients, or combinations thereof. The amount of agent within each unit is a therapeutically effective amount.

In embodiments of the present disclosure, the pharmaceutical compositions disclosed herein comprise an agent as described above in a total amount by weight of the composition of about 0.1% to about 95%. For example, the amount of the agent by weight of the pharmaceutical composition may be about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.1%, about 5.2%, about 5.3%, about 5.4%, about 5.5%, about 5.6%, about 5.7%, about 5.8%, about 5.9%, about 6%, about 6.1%, about 6.2%, about 6.3%, about 6.4%, about 6.5%, about 6.6%, about 6.7%, about 6.8%, about 6.9%, about 7%, about 7.1%, about 7.2%, about 7.3%, about 7.4%, about 7.5%, about 7.6%, about 7.7%, about 7.8%, about 7.9%, about 8%, about 8.1%, about 8.2%, about 8.3%, about 8.4%, about 8.5%, about 8.6%, about 8.7%, about 8.8%, about 8.9%, about 9%, about 9.1%, about 9.2%, about 9.3%, about 9.4%, about 9.5%, about 9.6%, about 9.7%, about 9.8%, about 9.9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90% or about 95%.

Where a range of values is provided herein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, an agent is a plasmid vector for introducing into a target cell for reproduction or transcription of an insert that comprises one or more nucleotide sequences that are carried within the plasmid vector. In some embodiments of the present disclosure, the plasmid vector is a viral vector. In some embodiments of the present disclosure, the vector is an adeno-associated virus vector.

As used herein, the term "nucleotide sequence" is intended to also include a human codon optimized variant.

In some embodiments of the present disclosure, the insert comprises one or more nucleotide sequences that encode for production of a protein. The protein is substantially similar, or substantially the same, as a translational product of a gene whose expression results in increased production of a Cetuximab-like protein (CLP) that can reduce or inhibit EGFR-mediated dysregulation of DNA synthesis of genes that relate to cell growth and proliferation in tumor cells. In some embodiments of the present disclosure, the CLP may be susceptible to one or more post-translational modification processes to create a CLP product that can bind with and inhibit EGFR. For clarity, references to CLP herein include references to the CLP product.

In some embodiments of the present disclosure, the CLP is substantially similar, or substantially the same, biofunctionality and bioavailability as Cetuximab that a subject could receive from an exogenous source.

The present disclosure relates to one or more agents, therapies, treatments, and methods of use of the agents and/or therapies and/or treatments for initiating or upregulating production of the CLP. Some embodiments of the present disclosure relate to methods for making a complex between at least one particle of an agent and at least one target cell of a subject for initiating or increasing production of the CLP within the subject. Therefore, the administration of the one or more vectors may increase the production of the precursor protein within one or more of a subject's cells. As such, the embodiments of the present disclosure can be used as a therapy or a treatment for a subject that has a condition whereby tumor cells have increased EGFR-mediated growth and proliferation.

In some embodiments of the present disclosure, the agent can be administered to the subject by an intravenous route, an intramuscular route, an intraperitoneal route, an intrathecal route, an intravesical route, a topical route, an intranasal route, a transmucosal route, a pulmonary route, and combinations thereof.

In some embodiments of the present disclosure, the agent can be administered to the subject by pipetting a dose of the agent into an in vitro cell culture, perfusing or immersing an ex vivo cell or tissue preparation with a solution that comprises the agent, mixing a biological fluid sample with a solution or substrate that comprises the agent, or combinations thereof.

Some embodiments of the present disclosure relate to an agent that can be administered to a subject with a condition that could benefit from an endogenous source of CLP. When a therapeutically effective amount of the agent is administered to the subject, one or more of the subject's cell may increase the translational production of the CLP.

In some embodiments of the present disclosure, the agent is a vector used for gene therapy. The gene therapy is useful for increasing the subject's endogenous production of the CLP. For example, the vector can contain one or more nucleotide sequences that that cause increased production of the CLP in the subject's cells where the vector is expressed.

In some embodiments of the present disclosure, the vector used for gene therapy is a virus that can be enveloped or not, replication effective or not, or combinations thereof. In some embodiments of the present disclosure, the vector is a virus that is not enveloped and not replication effective. In some embodiments of the present disclosure, the vector is a virus of the Paroviridae family. In some embodiments of the present disclosure, the vector is a virus of the genus *Dependoparvaovirus*. In some embodiments of the present disclosure, the vector is an adeno-associated virus (AAV). In some embodiments of the present disclosure, the vector is a recombinant AAV.

The embodiments of the present disclosure also relate to administering a therapeutically effective amount of the agent. In some embodiments of the present disclosure, the therapeutically effective amount of the agent that is administered to a patient is between about 10 and about $1\times10^{16}$ $TCID_{50}$/kg (50% tissue culture infective dose per kilogram of the patient's body weight). In some embodiments of the present disclosure, the therapeutically effective amount of the agent that is administered to the patient is about $1\times10^{13}$ $TCID_{50}$/kg. In some embodiments of the present disclosure, the therapeutically effective amount of the agent that is administered to a patient is measured in TPC/kg (total particle count of the agent per kilogram of the patient's body weight). In some embodiments the therapeutically effective amount of the agent is between about 10 and about $1\times10^{16}$ TCP/kg.

Some embodiments of the present disclosure relate to a method for making a complex within a subject. The method comprises a step of administering a therapeutically effective amount of the agent to the subject. The complex comprises at least one particle of the agent and one or more target cells. When the complex is formed, it affects a change in the metabolism of the one or more target cells, which results in the target cells starting and/or upregulating the production of the CLP. Examples of a target cell include but are not limited to: an innate immune cell, an acquired immune cell, an adrenal gland cell; a bile duct cell; a chondrocyte; a cochlear cell; a corneal cell; an endocardium cell; an endometrial cell; an endothelial cell; an epithelial cell; a fibroblast; a hair follicle cell; a hepatocyte; a lymph node cell; a mucosal cell; a myocyte; a neuron; a glomeruli cell; an optic nerve cell; an osteoblast; an ovarian tissue cell; a pancreatic islet beta cell; a pericardium cell; a platelet; a red blood cell (RBC); a retinal cell; a scleral cell; a Schwann cell; a T cell; a testicular tissue cell; a thyroid gland cell; a uveal cell; a tumor cell, or combinations thereof.

Some embodiments of the present disclosure relate to a therapy, or method of treating a condition, that can be administered to a subject with the condition. The therapy comprises a step of administering to the subject a therapeutically effective amount of an agent that will upregulate the subject's production of the CLP. The increased production of the CLP may result in increased levels of functional and bioavailable CLP, which may reduce deleterious effects of the condition upon the subject. For example, the CLP may reduce the development of new blood vessels in high metabolic-rate cells, such as tumor cells.

Below are examples of nucleotide sequences of each may be present in the insert. As will be appreciated by those skilled in the art, minor modifications, substitutions or replacements of a select few nucleotides or amino acids in the sequences provided below will not substantially impact the physiologic or biologic effect of such modified sequences, as compared to the sequences provided herein below. Any such modified sequences are also contemplated by the present disclosure as are all human codon optimized variants.

Some embodiments of the present disclosure relate to the following nucleotide sequence SEQ ID No. 1 (an inverted terminal repeat):

```
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact 120
aggggttcct                                                        130
```

Some embodiments of the present disclosure relate to the following nucleotide sequence SEQ ID No. 2 (an inverted terminal repeat):

```
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc 120
gagcgcgc                                                          128
```

Some embodiments of the present disclosure relate to the following nucleotide sequence SEQ ID No. 3 (a CASI promoter):

```
ggagttccgc gttacataac ttacggtaaa tggcccgcct ggctgaccgc ccaacgaccc  60
ccgcccattg acgtcaataa tgacgtatgt tcccatagta acgccaatag ggactttcca 120
ttgacgtcaa tgggtggagt atttacggta aactgcccac ttggcagtac atcaagtgta 180
```

-continued

```
tcatatgcca agtacgcccc ctattgacgt caatgacggt aaatggcccg cctggcatta  240
tgcccagtac atgaccttat gggactttcc tacttggcag tacatctacg tattagtcat  300
cgctattacc atggtcgagg tgagccccac gttctgcttc actctcccca tctccccccc  360
ctccccaccc ccaattttgt atttatttat tttttaatta ttttgtgcag cgatgggggc  420
gggggggggg gggggcgcgc gccaggcggg gcggggcggg gcgaggggcg gggcggggcg  480
aggcggagag gtgcggcggc agccaatcag agcggcgcgc tccgaaagtt tccttttatg  540
gcgaggcggc ggcggcggcg gccctataaa aagcgaagcg cgcggcgggc gggagtcgct  600
gcgcgctgcc ttcgccccgt gccccgctcc gccgccgcct cgcgccgccc gccccggctc  660
tgactgaccg cgttactaaa acaggtaagt ccggcctccg cgccgggttt tggcgcctcc  720
cgcgggcgcc cccctcctca cggcgagcgc tgccacgtca gacgaagggc gcagcgagcg  780
tcctgatcct tccgcccgga cgctcaggac agcggcccgc tgctcataag actcggcctt  840
agaaccccag tatcagcaga aggacatttt aggacgggac ttgggtgact ctagggcact  900
ggttttcttt ccagagagcg gaacaggcga ggaaaagtag tcccttctcg gcgattctgc  960
ggagggatct ccgtggggcg gtgaacgccg atgatgcctc tactaaccat gttcatgttt 1020
tctttttttt tctacaggtc ctgggtgacg aacag                            1055
```

Some embodiments of the present disclosure relate to the following nucleotide sequence SEQ ID No. 4 (a variable heavy-chain portion):

```
caggtacaac tgaaacaaag cgggcctggg ctggtccagc catcccaaag tttgtccata  60
acttgcactg ttagtggttt tagcttgacc aattacgggg tgcattgggt aagacagagt 120
cctggtaagg gcctcgaatg gctgggcgtg atatggtcag gcggcaatac tgactacaat 180
actccattta ccagcagatt gtccatcaat aaagataatt ctaaaagcca ggtattcttt 240
aagatgaact ctctgcagtc caatgatact gcaatttatt actgtgcccg agcacttacc 300
tactacgatt acgagttcgc atactggggc cagggtaccc tcgtgaccgt atctgcagcg 360
```

Some embodiments of the present disclosure relate to the following nucleotide sequence SEQ ID No. 5 (a variable light-chain portion):

```
gatatccttc tgactcaatc ccctgtgatt ctgtcagtgt caccagggga aagggtcagt  60
ttttcatgtc gcgcatctca aagcattggc actaacatcc actggtacca acaacgcaca 120
aacggaagtc cccgcttgct catcaagtat gcaagcgaat caatcagcgg gatcccttcc 180
aggttcagtg gtagtgggag tggtacagat ttcactctct caattaacag cgtagagtcc 240
gaggacatcg ccgactatta ttgccaacag aacaacaact ggcctactac atttggtgcc 300
ggtacaaaac tggagcttaa acgc                                        324
```

Some embodiments of the present disclosure relate to the following nucleotide sequence SEQ ID No. 6 (a human IgG-1 constant heavy-chain portion):

```
agcaccaagg gcccatcggt cttccccctg gcaccctcct ccaagagcac ctctgggggc  60
acagcggccc tgggctgcct ggtcaaggac tacttccccg aaccggtgac ggtgtcgtgg 120
aactcaggcg ccctgaccag cggcgtgcac accttcccgg ctgtcctaca gtcctcagga 180
```

-continued

```
ctctactccc tcagcagcgt ggtgaccgtg ccctccagca gcttgggcac ccagacctac 240
atctgcaacg tgaatcacaa gcccagcaac accaaggtgg acaagaaagt tgagcccaaa 300
tcttgtgaca aaactcacac atgcccaccg tgcccagcac ctgaactcct ggggggaccg 360
tcagtcttcc tcttcccccc anaacccaag gacaccctca tgatctcccg gacccctgag 420
gtcacatgcg tggtggtgga cgtgagccac gaagaccctg aggtcaagtt caactggtac 480
gtggacggcg tggaggtgca taatgccaag acaaagccgc gggaggagca gtacaacagc 540
acgtaccgtg tggtcagcgt cctcaccgtc ctgcaccagg actggctgaa tggcaaggag 600
tacaagtgca aggtctccaa caaagccctc ccagccccca tcgagaaaac catctccaaa 660
gccaaagggc agccccgaga accacaggtg tacaccctgc ccccatcccg ggaggagatg 720
accaagaacc aggtcagcct gacctgcctg gtcaaaggct tctatcccag cgacatcgcc 780
gtggagtggg agagcaatgg gcagccggag aacaactaca agaccacgcc tcccgtgctg 840
gactccgacg gctccttctt cctctacagc aagctcaccg tggacaagag caggtggcag 900
caggggaacg tcttctcatg ctccgtgatg catgaggctc tgcacaacca ctacacgcag 960
aagagcctct ccctgtctcc gggtaaa                                    987
```

Some embodiments of the present disclosure relate to the following nucleotide sequence SEQ ID No. 7 (a human IgG-1 Kappa light-chain portion):

```
ggtcagccca aggctgcccc ctcggtcact ctgttcccgc cctcctctga ggagcttcaa  60
gccaacaagg ccacactggt gtgtctcata agtgacttct acccgggagc cgtgacagtg 120
gcctggaagg cagatagcag ccccgtcaag gcgggagtgg agaccaccac accctccaaa 180
caaagcaaca acaagtacgc ggccagcagc tatctgagcc tgacgcctga gcagtggaag 240
tcccacagaa gctacagctg ccaggtcacg catgaaggga gcaccgtgga gaagacagtg 300
gcccctacag aatgttcata g                                          321
```

Some embodiments of the present disclosure relate to the following nucleotide sequence SEQ ID No. 8 (a Woodchuck Hepatitis Posttranslational Regulatory Element (WPRE) portion):

```
aatcaacctc tggattacaa aatttgtgaa agattgactg gtattcttaa ctatgttgct  60
ccttttacgc tatgtggata cgctgcttta atgcctttgt atcatgctat tgcttcccgt 120
atggctttca ttttctcctc cttgtataaa tcctggttgc tgtctcttta tgaggagttg 180
tggcccgrtg tcaggcaacg tggcgtggtg tgcactgtgt ttgctgacgc aacccccact 240
ggttggggca ttgccaccac ctgtcagctc ctttccggga ctttcgcttt ccccctccct 300
attgccacgg cggaactcat cgccgcctgc cttgcccgct gctggacagg ggctcggctg 360
ttgggcactg acaattccgt ggtgttgtcg gggaaatcat cgtcctttcc ttggctgctc 420
gcctgtgttg ccacctggat tctgcgcggg acgtccttct gctacgtccc ttcggccctc 480
aatccagcgg accttccttc ccgcggcctg ctgccggctc tgcggcctct tccgcgtctt 540
cgccttcgcc ctcagacgag tcggatctcc ctttgggccg cctccccgc             589
```

Some embodiments of the present disclosure relate to the following nucleotide sequence SEQ ID No. 9 (an AAV vector):

```
ctgcgcgctc gctcgctcac tgaggccgcc cgggcaaagc ccgggcgtcg ggcgaccttt   60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggacattga ttattgacta gtggagttcc gcgttacata acttacggta aatggcccgc  240
ctggctgacc gcccaacgac ccccgcccat tgacgtcaat aatgacgtat gttcccatag  300
taacgccaat agggactttc cattgacgtc aatgggtgga gtatttacgg taaactgccc  360
acttggcagt acatcaagtg tatcatatgc caagtacgcc ccctattgac gtcaatgacg  420
gtaaatggcc cgcctggcat tatgcccagt acatgacctt atgggacttt cctacttggc  480
agtacatcta cgtattagtc atcgctatta ccatggtcga ggtgagcccc acgttctgct  540
tcactctccc catctccccc ccctccccac ccccaatttt gtatttattt atttttaat   600
tattttgtgc agcgatgggg gcgggggggg ggggggggcgc gcgccaggcg gggcggggcg  660
gggcgagggg cggggcgggg cgaggcggag aggtgcggcg gcagccaatc agagcggcgc  720
gctccgaaag tttcctttta tggcgaggcg gcggcggcgg cggccctata anaagcgaag  780
cgcgcggcgg gcgggagtcg ctgcgcgctg ccttcgcccc gtgccccgct ccgccgccgc  840
ctcgcgccgc ccgccccggc tctgactgac cgcgttacta aaacaggtaa gtccggcctc  900
cgcgccgggt tttggcgcct cccgcgggcg ccccccctcct cacggcgagc gctgccacgt  960
cagacgaagg gcgcagcgag cgtcctgatc cttccgcccg gacgctcagg acagcggccc 1020
gctgctcata agactcggcc ttagaacccc agtatcagca gaaggacatt ttaggacggg 1080
acttgggtga ctctagggca ctggttttct ttccagagag cggaacaggc gaggaaaagt 1140
agtcccttct cggcgattct gcggagggat ctccgtgggg cggtgaacgc cgatgatgcc 1200
tctactaacc atgttcatgt tttctttttt tttctacagg tcctgggtga cgaacagggt 1260
accgccacca tggcgacggg ttcaagaact tccctacttc ttgcatttgg cctgctttgt 1320
ttgccgtggt tacaggaggg ctcggcacag gtacaactga aacaaagcgg gcctgggctg 1380
gtccagccat cccaaagttt gtccataact tgcactgtta gtggttttag cttgaccaat 1440
tacggggtgc attgggtaag acagagtcct ggtaagggcc tcgaatggct gggcgtgata 1500
tggtcaggcg gcaatactga ctacaatact ccatttacca gcagattgtc catcaataaa 1560
gataattcta aaagccaggt attctttaag atgaactctc tgcagtccaa tgatactgca 1620
atttattact gtgcccgagc acttacctac tacgattacg agttcgcata ctggggccag 1680
ggtaccctcg tgaccgtatc tgcagcgagc accaagggcc catcggtctt ccccctggca 1740
ccctcctcca agagcacctc tgggggcaca gcggccctgg gctgcctggt caaggactac 1800
ttccccgaac cggtgacggt gtcgtggaac tcaggcgccc tgaccagcgg cgtgcacacc 1860
ttcccggctg tcctacagtc ctcaggactc tactccctca gcagcgtggt gaccgtgccc 1920
tccagcagct tgggcaccca gacctacatc tgcaacgtga atcacaagcc cagcaacacc 1980
aaggtggaca agaaagttga gcccaaatct tgtgacaaaa ctcacacatg cccaccgtgc 2040
ccagcacctg aactcctggg gggaccgtca gtcttcctct tccccccaaa acccaaggac 2100
accctcatga tctcccggac ccctgaggtc acatgcgtgg tggtggacgt gagccacgaa 2160
gaccctgagg tcaagttcaa ctggtacgtg gacggcgtgg aggtgcataa tgccaagaca 2220
aagccgcggg aggagcagta caacagcacg taccgtgtgg tcagcgtcct caccgtcctg 2280
```

-continued caccaggact ggctgaatgg caaggagtac aagtgcaagg tctccaacaa agccctccca 2340
gcccccatcg agaaaaccat ctccaaagcc aaagggcagc cccgagaacc acaggtgtac 2400
accctgcccc catcccggga ggagatgacc aagaaccagg tcagcctgac ctgcctggtc 2460
aaaggcttct atcccagcga catcgccgtg gagtgggaga gcaatgggca gccggagaac 2520
aactacaaga ccacgcctcc cgtgctggac tccgacggct ccttcttcct ctacagcaag 2580
ctcaccgtgg acaagagcag gtggcagcag gggaacgtct tctcatgctc cgtgatgcat 2640
gaggctctgc acaaccacta cacgcagaag agcctctccc tgtctccggg taaacgaaaa 2700
agaagatcag gttcgggtgc gccagtaaag cagacattaa actttgattt gctgaaactt 2760
gcaggtgatg tagagtcaaa tccaggtcca atggcaacag ggagccgaac ctctctgctc 2820
cttgctttcg ggctcctttg cctaccgtgg ctccaagagg gctcggcaga tatccttctg 2880
actcaatccc ctgtgattct gtcagtgtca ccaggggaaa gggtcagttt ttcatgtcgc 2940
gcatctcaaa gcattggcac taacatccac tggtaccaac aacgcacaaa cggaagtccc 3000
cgcttgctca tcaagtatgc aagcgaatca atcagcggga tcccttccag gttcagtggt 3060
agtgggagtg gtacagattt cactctctca attaacagcg tagagtccga ggacatcgcc 3120
gactattatt gccaacagaa caacaactgg cctactacat ttggtgccgg tacaaaactg 3180
gagcttaaac gcggtcagcc caaggctgcc ccctcggtca ctctgttccc gccctcctct 3240
gaggagcttc aagccaacaa ggccacactg gtgtgtctca taagtgactt ctacccggga 3300
gccgtgacag tggcctggaa ggcagatagc agccccgtca aggcgggagt ggagaccacc 3360
acaccctcca aacaaagcaa caacaagtac gcggccagca gctatctgag cctgacgcct 3420
gagcagtgga agtcccacag aagctacagc tgccaggtca cgcatgaagg gagcaccgtg 3480
gagaagacag tggcccctac agaatgttca tagtctagaa taatcaacct ctggattaca 3540
aaatttgtga aagattgact ggtattctta actatgttgc tccttttacg ctatgtggat 3600
acgctgcttt aatgcctttg tatcatgcta ttgcttcccg tatggctttc attttctcct 3660
ccttgtataa atcctggttg ctgtctcttt atgaggagtt gtggcccgtt gtcaggcaac 3720
gtggcgtggt gtgcactgtg tttgctgacg caacccccac tggttggggc attgccacca 3780
cctgtcagct cctttccggg actttcgctt tccccctccc tattgccacg gcggaactca 3840
tcgccgcctg ccttgcccgc tgctggacag gggctcggct gttgggcact gacaattccg 3900
tggtgttgtc ggggaaatca tcgtcctttc cttggctgct cgcctgtgtt gccacctgga 3960
ttctgcgcgg gacgtccttc tgctacgtcc cttcggccct caatccagcg gaccttcctt 4020
cccgcggcct gctgccggct ctgcggcctc ttccgcgtct tcgccttcgc cctcagacga 4080
gtcggatctc cctttgggcc gcctccccgc ctaagcttat cgataccgtc gagatctaac 4140
ttgtttattg cagcttataa tggttacaaa taaagcaata gcatcacaaa tttcacaaat 4200
aaagcatttt tttcactgca ttctagttgt ggtttgtcca aactcatcaa tgtatcttat 4260
catgtctgga tctcgacctc gactagagca tggctacgta gataagtagc atggcgggtt 4320
aatcattaac tacaaggaac ccctagtgat ggagttggcc actccctctc tgcgcgctcg 4380
ctcgctcact gaggccgggc gaccaaaggt cgcccgacgc ccgggctttg cccgggcggc 4440
ctcagtgagc gagcgagcgc gccagctggc gtaatagcga agaggcccgc accgatcgcc 4500
cttcccaaca gttgcgcagc ctgaatggcg aatggaattc cagacgattg agcgtcaaaa 4560
tgtaggtatt tccatgagcg tttttcctgt tgcaatggct ggcggtaata ttgttctgga 4620
tattaccagc aaggccgata gtttgagttc ttctactcag gcaagtgatg ttattactaa 4680
tcaaagaagt attgcgacaa cggttaattt gcgtgatgga cagactcttt tactcggtgg 4740

-continued

```
cctcactgat tataaaaaca cttctcagga ttctggcgta ccgttcctgt ctaaaatccc 4800
tttaatcggc ctcctgttta gctcccgctc tgattctaac gaggaaagca cgttatacgt 4860
gctcgtcaaa gcaaccatag tacgcgccct gtagcggcgc attaagcgcg gcgggtgtgg 4920
tggttacgcg cagcgtgacc gctacacttg ccagcgccct agcgcccgct cctttcgctt 4980
tcttcccttc ctttctcgcc acgttcgccg gctttccccg tcaagctcta aatcgggggc 5040
tccctttagg gttccgattt agtgctttac ggcacctcga ccccaaaaaa cttgattagg 5100
gtgatggttc acgtagtggg ccatcgccct gatagacggt ttttcgccct ttgacgttgg 5160
agtccacgtt ctttaatagt ggactcttgt tccaaactgg aacaacactc aaccctatct 5220
cggtctattc ttttgattta taagggattt tgccgatttc ggcctattgg ttaaaaaatg 5280
agctgattta acaaaaattt aacgcgaatt ttaacaaaat attaacgttt acaatttaaa 5340
tatttgctta tacaatcttc ctgtttttgg ggcttttctg attatcaacc ggggtacata 5400
tgattgacat gctagtttta cgattaccgt tcatcgattc tcttgtttgc tccagactct 5460
caggcaatga cctgatagcc tttgtagaga cctctcaaaa atagctaccc tctccggcat 5520
gaatttatca gctagaacgg ttgaatatca tattgatggt gatttgactg tctccggcct 5580
ttctcacccg tttgaatctt tacctacaca ttactcaggc attgcattta aaatatatga 5640
gggttctaaa aatttttatc cttgcgttga aataaaggct tctcccgcaa aagtattaca 5700
gggtcataat gtttttggta caaccgattt agctttatgc tctgaggctt tattgcttaa 5760
ttttgctaat tctttgcctt gcctgtatga tttattggat gttggaattc ctgatgcggt 5820
attttctcct tacgcatctg tgcggtattt cacaccgcat atggtgcact ctcagtacaa 5880
tctgctctga tgccgcatag ttaagccagc cccgacaccc gccaacaccc gctgacgcgc 5940
cctgacgggc ttgtctgctc ccggcatccg cttacagaca agctgtgacc gtctccggga 6000
gctgcatgtg tcagaggttt tcaccgtcat caccgaaacg cgcgagacga aagggcctcg 6060
tgatacgcct atttttatag gttaatgtca tgataataat ggtttcttag acgtcaggtg 6120
gcacttttcg gggaaatgtg cgcggaaccc ctatttgttt atttttctaa atacattcaa 6180
atatgtatcc gctcatgaga caataaccct gataaatgct tcaataatat tgaaaaagga 6240
agagtatgag tattcaacat ttccgtgtcg cccttattcc cttttttgcg gcattttgcc 6300
ttcctgtttt tgctcaccca gaaacgctgg tgaaagtaaa agatgctgaa gatcagttgg 6360
gtgcacgagt gggttacatc gaactggatc tcaacagcgg taagatcctt gagagttttc 6420
gccccgaaga acgttttcca atgatgagca cttttaaagt tctgctatgt ggcgcggtat 6480
tatcccgtat tgacgccggg caagagcaac tcggtcgccg catacactat tctcagaatg 6540
acttggttga gtactcacca gtcacagaaa agcatcttac ggatggcatg acagtaagag 6600
aattatgcag tgctgccata accatgagtg ataacactgc ggccaactta cttctgacaa 6660
cgatcggagg accgaaggag ctaaccgctt ttttgcacaa catgggggat catgtaactc 6720
gccttgatcg ttgggaaccg gagctgaatg aagccatacc aaacgacgag cgtgacacca 6780
cgatgcctgt agcaatggca acaacgttgc gcaaactatt aactggcgaa ctacttactc 6840
tagcttcccg gcaacaatta atagactgga tggaggcgga taaagttgca ggaccacttc 6900
tgcgctcggc ccttccggct ggctggttta ttgctgataa atctggagcc ggtgagcgtg 6960
ggtctcgcgg tatcattgca gcactggggc cagatggtaa gccctcccgt atcgtagtta 7020
tctacacgac ggggagtcag gcaactatgg atgaacgaaa tagacagatc gctgagatag 7080
gtgcctcact gattaagcat tggtaactgt cagaccaagt ttactcatat atactttaga 7140
```

-continued

```
ttgatttaaa acttcatttt taatttaaaa ggatctaggt gaagatcctt tttgataatc 7200

tcatgaccaa aatcccttaa cgtgagtttt cgttccactg agcgtcagac cccgtagaaa 7260

agatcaaagg atcttcttga gatccttttt ttctgcgcgt aatctgctgc ttgcaaacaa 7320

aaaaaccacc gctaccagcg gtggtttgtt tgccggatca agagctacca actctttttc 7380

cgaaggtaac tggcttcagc agagcgcaga taccaaatac tgtccttcta gtgtagccgt 7440

agttaggcca ccacttcaag aactctgtag caccgcctac atacctcgct ctgctaatcc 7500

tgttaccagt ggctgctgcc agtggcgata agtcgtgtct taccgggttg gactcaagac 7560

gatagttacc ggataaggcg cagcggtcgg gctgaacggg gggttcgtgc acacagccca 7620

gcttggagcg aacgacctac accgaactga gatacctaca gcgtgagcta tgagaaagcg 7680

ccacgcttcc cgaagggaga aaggcggaca ggtatccggt aagcggcagg gtcggaacag 7740

gagagcgcac gagggagctt ccagggggaa acgcctggta tctttatagt cctgtcgggt 7800

ttcgccacct ctgacttgag cgtcgatttt tgtgatgctc gtcagggggg cggagcctat 7860

ggaaaaacgc cagcaacgcg gcctttttac ggttcctggc cttttgctgg ccttttgctc 7920

acatgttctt tcctgcgtta tcccctgatt ctgtggataa ccgtattacc gcctttgagt 7980

gagctgatac cgctcgccgc agccgaacga ccgagcgcag cgagtcagtg agcgaggaag 8040

cggaagagcg cccaatacgc aaaccgcctc tccccgcgcg ttggccgatt cattaatgca 8100

gcag                                                              8104
```

Some embodiments of the present disclosure relate to the insert that comprises the nucleotide sequences: SEQ ID No. 1, SEQ ID No. 2, SEQ ID No. 3, SEQ ID No. 4, SEQ ID No. 5, SEQ ID No. 6, SEQ ID No. 7, SEQ ID No. 8 or combinations thereof. Some embodiments of the present disclosure relate to the insert that comprises the nucleotide sequences: SEQ ID No. 4 and SEQ ID No. 7.

Some embodiments of the present disclosure relate to a composition of matter and/or the agent that comprises the nucleotide sequence of SEQ ID No. 9.

The nucleotide sequence encoding the CLP or a sub-peptide thereof may be linked directly or indirectly to the nucleotide sequence encoding the immunoglobulin. By "directly", it is meant that the sequences are continuous without intervening nucleotides. By "indirectly", it is meant that there are intervening nucleotides. The intervening nucleotides may, for example, be a linker peptide and/or a hinge peptide. In an embodiment, there are nucleotides encoding a flexible linker peptide and a hinge peptide positioned between nucleotide sequence encoding the CLP or sub-peptide thereof and the nucleotide sequence encoding the immunoglobulin.

Example 1—Expression Cassette

Expression cassettes for expressing the CLP in a subject cell were synthesized by Genscript. Each cassette contained a signal peptide, the precursor protein that may be followed by a self-cleaving 2A peptide sequence, a signal peptide and the human lambda constant domain. The synthesized CLP expression cassettes were cloned into the pAVA-00200 plasmid backbone containing the CASI promoter1, multiple cloning site (MCS), Woodchuck Hepatitis Virus post-transcriptional regulatory element (WPRE), Simian virus 40 (SV40) polyadenylation (polyA) sequence all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each CLP expression cassette was amplified by PCR using Taq polymerase and the PCR products were gel purified and the bands on interest were also excised and purified using a gel extraction kit. These PCR products contained the CLP expression cassettes in addition to 15 base pair 5' and 3' overhangs that align with the ends of the linearized pAVA-00200 backbone. Using in-fusion cloning2, the amplified CLP expression cassettes are integrated with the pAVA-00200 backbone via homologous recombination. The resulting plasmid vectors contained at least the following: 5' ITR, a CASI promoter, the CLP expression cassette, WPRE, and a 3' ITR, per SEQ ID No. 9.

Example 2—Experimental Data

The ovarian bursa of C57BL/6 mice were implanted with $1\times10^6$ ID8 epithelial carcinoma cells. About 60 days later, eight mice were administered i.p. 50 mM phosphate buffered saline (control group) or $1\times10^{11}$ vg of the AAV comprising SEQ ID No. 9 (treatment group).

The serum samples were analyzed using a quantitative ELISA to measure human IgG-1 levels (as an indicator of CLP production). The analysis of the serum samples from the animals in the control group showed that no human IgG-1 was detected. FIG. 1 shows experimental human IgG CLP expression data, as an indirect measure of CLP expression obtained from the treatment group. Without being bound by any particular theory, the mice in the treatment group expressed CLP up to 28 days following administration of the AAV vector that comprised the SEQ ID No. 9.

The invention claimed is:

1. A recombinant virus vector (RVV), the RVV comprising a nucleotide sequence encoding for production of a cetuximab-like protein (CLP), wherein the nucleotide sequence comprises SEQ ID No: 1, SEQ ID No: 2, SEQ ID No: 3, SEQ ID No: 4, SEQ ID No.5, SEQ ID No: 6, SEQ ID No. 7 and SEQ ID No. 8, wherein the RVV is an adeno-associated virus vector and wherein the CLP can bind to and inhibit the activity of Epidermanl Growth Factor Receptor (EGFR).

2. The RVV of claim 1, wherein the inhibited activity of the EGFR is EGFR-mediated dysregulation of DNA synthesis of genes that relate to cell growth and proliferation in tumor cells.

3. A pharmaceutical composition comprising the RVV of claim 1 and one or more pharmaceutically acceptable carriers and/or one or more excipients.

4. A method of making an agent/target cell complex, the method comprising a step of administering an adeno-associated virus (AAV) to a target cell for forming the agent/target cell complex, wherein the agent/target cell complex causes the target cell to increase production of a cetuximab-like protein (CLP), wherein the AAV comprises the nucleotide sequence according to SEQ ID No. 9 for increasing the target cell's production of the CLP.

5. The method of claim 4, wherein the target cell is one or more of an adrenal gland cell; a bile duct cell; a chondrocyte; a cochlear cell; a corneal cell; an endocardium cell; an endometrial cell; an endothelial cell; an epithelial cell; a fibroblast; a hair follicle cell; a hepatocyte; a lymph node cell; a mucosal cell; a myocyte; a neuron; a glomeruli cell; an optic nerve cell; an osteoblast; an ovarian tissue cell; a pancreatic islet beta cell; a pericardium cell; a platelet; a red blood cell (RBC); a retinal cell; a scleral cell; a Schwann cell; a T cell; a testicular tissue cell; a thyroid gland cell; a uveal cell; a tumor cell, and combinations thereof.

* * * * *

SEQUENCE LISTING

```
Sequence total quantity: 9
SEQ ID NO: 1            moltype = DNA  length = 130
FEATURE                 Location/Qualifiers
misc_feature            1..130
                        note = Synthetic Sequence
source                  1..130
                        mol_type = other DNA
                        organism = synthetic construct
SEQUENCE: 1
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct                                                         130

SEQ ID NO: 2            moltype = DNA  length = 128
FEATURE                 Location/Qualifiers
misc_feature            1..128
                        note = Synthetic Sequence
source                  1..128
                        mol_type = other DNA
                        organism = synthetic construct
SEQUENCE: 2
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgc                                                           128

SEQ ID NO: 3            moltype = DNA  length = 1055
FEATURE                 Location/Qualifiers
misc_feature            1..1055
                        note = Synthetic Sequence
source                  1..1055
                        mol_type = other DNA
                        organism = synthetic construct
SEQUENCE: 3
ggagttccgc gttacataac ttacggtaaa tggcccgcct ggctgaccgc ccaacgaccc  60
ccgcccattg acgtcaataa tgacgtatgt tcccatagta acgccaatag ggactttcca  120
ttgacgtcaa tgggtggagt atttacggta aactgcccac ttggcagtac atcaagtgta  180
tcatatgcca agtacgcccc ctattgacgt caatgacggt aaatggcccg cctggcatta  240
tgcccagtac atgaccttat gggactttcc tacttggcag tacatctacg tattagtcat  300
cgctattacc atggtcgagg tgagccccac gttctgcttc actctcccca tctccccccc  360
ctccccaccc ccaattttgt atttatttat tttttaatta ttttgtgcag cgatgggggc  420
gggggggggg ggggggcgcgc gccaggcggg gcggggcggg gcgaggggcg gggcggggcg  480
aggcggagag gtgcggcggc agccaatcag agcggcgcgc tccgaaagtt tccttttatg  540
gcgaggcggc ggcggcggcg gccctataaa aagcgaagcg cgcggcgggc gggagtcgct  600
gcgcgctgcc ttcgccccgt gccccgctcc gccgccgcct cgcgccgccc gccccggctc  660
tgactgaccg cgttactaaa acaggtaagt ccggcctccg cgccgggttt tggcgcctcc  720
cgcgggcgcc cccctcctca cggcgagcgc tgccacgtca gacgaagggc gcagcgagcg  780
tcctgatcct tccgcccgga cgctcaggac agcggcccgc tgctcataag actcggcctt  840
agaaccccag tatcagcaga aggacatttt aggacgggac ttgggtgact ctagggcact  900
ggttttcttt ccagagagcg gaacaggcga ggaaaagtag tcccttctcg gcgattctgc  960
ggagggatct ccgtggggcg gtgaacgccg atgatgcctc tactaaccat gttcatgttt  1020
tctttttttt tctacaggtc ctgggtgacg aacag                             1055

SEQ ID NO: 4            moltype = DNA  length = 360
FEATURE                 Location/Qualifiers
misc_feature            1..360
                        note = Synthetic Sequence
source                  1..360
                        mol_type = other DNA
                        organism = synthetic construct
SEQUENCE: 4
caggtacaac tgaaacaaag cgggcctggg ctggtccagc catcccaaag tttgtccata  60
acttgcactg ttagtggttt tagcttgacc aattacgggg tgcattgggt aagacagagt  120
cctggtaagg gcctcgaatg gctgggcgtg atatggtcag gcggcaatac tgactacaat  180
actccattta ccagcagatt gtccatcaat aaagataatt ctaaaagcca ggtattcttt  240
aagatgaact ctctgcagtc caatgatact gcaatttatt actgtgcccg agcacttacc  300
tactacgatt acgagttcgc atactggggc cagggtaccc tcgtgaccgt atctgcagcg  360

SEQ ID NO: 5            moltype = DNA  length = 324
FEATURE                 Location/Qualifiers
misc_feature            1..324
                        note = Synthetic Sequence
source                  1..324
                        mol_type = other DNA
                        organism = synthetic construct
SEQUENCE: 5
gatatccttc tgactcaatc ccctgtgatt ctgtcagtgt caccagggga aagggtcagt  60
ttttcatgtc gcgcatctca aagcattggc actaacatcc actggtacca acaacgcaca  120
aacggaagtc cccgcttgct catcaagtat gcaagcgaat caatcagcgg gatcccttcc  180
```

-continued

```
aggttcagtg gtagtgggag tggtacagat ttcactctct caattaacag cgtagagtcc  240
gaggacatcg ccgactatta ttgccaacag aacaacaact ggcctactac atttggtgcc  300
ggtacaaaac tggagcttaa acgc                                         324

SEQ ID NO: 6           moltype = DNA  length = 987
FEATURE                Location/Qualifiers
misc_feature           1..987
                       note = Synthetic Sequence
source                 1..987
                       mol_type = other DNA
                       organism = synthetic construct
SEQUENCE: 6
agcaccaagg gcccatcggt cttccccctg gcaccctcct ccaagagcac ctctgggggc  60
acagcggccc tgggctgcct ggtcaaggac tacttccccg aaccggtgac ggtgtcgtgg  120
aactcaggcg ccctgaccag cggcgtgcac accttcccgg ctgtcctaca gtcctcagga  180
ctctactccc tcagcagcgt ggtgaccgtg ccctccagca gcttgggcac ccagacctac  240
atctgcaacg tgaatcacaa gcccagcaac accaaggtgg acaagaaagt tgagcccaaa  300
tcttgtgaca aaactcacac atgcccaccg tgcccagcac ctgaactcct ggggggaccg  360
tcagtcttcc tcttcccccc aaaacccaag gacaccctca tgatctcccg gacccctgag  420
gtcacatgcg tggtggtgga cgtgagccac gaagaccctg aggtcaagtt caactggtac  480
gtggacggcg tggaggtgca taatgccaag acaaagccgc gggaggagca gtacaacagc  540
acgtaccgtg tggtcagcgt cctcaccgtc ctgcaccagg actggctgaa tggcaaggag  600
tacaagtgca aggtctccaa caaagccctc ccagccccca tcgagaaaac catctccaaa  660
gccaaagggc agccccgaga accacaggtg tacaccctgc ccccatcccg ggaggagatg  720
accaagaacc aggtcagcct gacctgcctg gtcaaaggct tctatcccag cgacatcgcc  780
gtggagtggg agagcaatgg gcagccggag aacaactaca agaccacgcc tcccgtgctg  840
gactccgacg gctccttctt cctctacagc aagctcaccg tggacaagag caggtggcag  900
caggggaacg tcttctcatg ctccgtgatg catgaggctc tgcacaacca ctacacgcag  960
aagagcctct ccctgtctcc gggtaaa                                      987

SEQ ID NO: 7           moltype = DNA  length = 321
FEATURE                Location/Qualifiers
misc_feature           1..321
                       note = Synthetic Sequence
source                 1..321
                       mol_type = other DNA
                       organism = synthetic construct
SEQUENCE: 7
ggtcagccca aggctgcccc ctcggtcact ctgttcccgc cctcctctga ggagcttcaa  60
gccaacaagg ccacactggt gtgtctcata agtgacttct acccgggagc cgtgacagtg  120
gcctggaagg cagatagcag ccccgtcaag gcgggagtgg agaccaccac accctccaaa  180
caaagcaaca acaagtacgc ggccagcagc tatctgagcc tgacgcctga gcagtggaag  240
tcccacagaa gctacagctg ccaggtcacg catgaaggga gcaccgtgga gaagacagtg  300
gcccctacag aatgttcata g                                            321

SEQ ID NO: 8           moltype = DNA  length = 589
FEATURE                Location/Qualifiers
misc_feature           1..589
                       note = Synthetic Sequence
source                 1..589
                       mol_type = other DNA
                       organism = synthetic construct
SEQUENCE: 8
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgc               589

SEQ ID NO: 9           moltype = DNA  length = 8104
FEATURE                Location/Qualifiers
misc_feature           1..8104
                       note = Synthetic Sequence
source                 1..8104
                       mol_type = other DNA
                       organism = synthetic construct
SEQUENCE: 9
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggacattga ttattgacta gtggagttcc gcgttacata acttacggta aatggcccgc  240
ctggctgacc gcccaacgac ccccgcccat tgacgtcaat aatgacgtat gttcccatag  300
taacgccaat agggactttc cattgacgtc aatgggtgga gtatttacgg taaactgccc  360
acttggcagt acatcaagtg tatcatatgc caagtacgcc ccctattgac gtcaatgacg  420
```

-continued

```
gtaaatggcc cgcctggcat tatgcccagt acatgacctt atgggacttt cctacttggc  480
agtacatcta cgtattagtc atcgctatta ccatggtcga ggtgagcccc acgttctgct  540
tcactctccc catctccccc ccctccccac ccccaatttt gtatttattt atttttaat   600
tattttgtgc agcgatgggg gcgggggggg ggggggggcgc gcgccaggcg gggcggggcg  660
gggcgagggg cggggcgggg cgaggcggag aggtgcggcg gcagccaatc agagcggcgc  720
gctccgaaag tttcctttta tggcgaggcg gcggcggcgg cggccctata aaaagcgaag  780
cgcgcggcgg gcgggagtcg ctgcgcgctg ccttcgcccc gtgccccgct ccgccgccgc  840
ctcgcgccgc ccgccccggc tctgactgac cgcgttacta aaacaggtaa gtccggcctc  900
cgcgccgggt tttggcgcct cccgcgggcg cccccctcct cacggcgagc gctgccacgt  960
cagacgaagg gcgcagcgag cgtcctgatc cttccgcccg gacgctcagg acagcggccc  1020
gctgctcata agactcggcc ttagaacccc agtatcagca gaaggacatt ttaggacggg  1080
acttgggtga ctctagggca ctggttttct ttccagagag cggaacaggc gaggaaaagt  1140
agtcccttct cggcgattct gcggagggat ctccgtgggg cggtgaacgc cgatgatgcc  1200
tctactaacc atgttcatgt tttctttttt tttctacagg tcctgggtga cgaacagggt  1260
accgccacca tggcgacggg ttcaagaact tccctacttc ttgcatttgg cctgctttgt  1320
ttgccgtggt tacaggaggg ctcggcacag gtacaactga aacaaagcgg gcctgggctg  1380
gtccagccat cccaaagttt gtccataact tgcactgtta gtggttttag cttgaccaat  1440
tacggggtgc attgggtaag acagagtcct ggtaagggcc tcgaatggct gggcgtgata  1500
tggtcaggcg gcaatactga ctacaatact ccatttacca gcagattgtc catcaataaa  1560
gataattcta aaagccaggt attctttaag atgaactctc tgcagtccaa tgatactgca  1620
atttattact gtgcccgagc acttacctac tacgattacg agttcgcata ctggggccag  1680
ggtaccctcg tgaccgtatc tgcagcgagc accaagggcc catcggtctt ccccctggca  1740
ccctcctcca agagcacctc tgggggcaca gcggccctgg gctgcctggt caaggactac  1800
ttccccgaac cggtgacggt gtcgtggaac tcaggcgccc tgaccagcgg cgtgcacacc  1860
ttcccggctg tcctacagtc ctcaggactc tactccctca gcagcgtggt gaccgtgccc  1920
tccagcagct tgggcaccca gacctacatc tgcaacgtga atcacaagcc cagcaacacc  1980
aaggtggaca agaaagttga gcccaaatct tgtgacaaaa ctcacacatg cccaccgtgc  2040
ccagcacctg aactcctggg gggaccgtca gtcttcctct tccccccaaa acccaaggac  2100
accctcatga tctcccggac ccctgaggtc acatgcgtgg tggtggacgt gagccacgaa  2160
gaccctgagg tcaagttcaa ctggtacgtg gacggcgtgg aggtgcataa tgccaagaca  2220
aagccgcggg aggagcagta caacagcacg taccgtgtgg tcagcgtcct caccgtcctg  2280
caccaggact ggctgaatgg caaggagtac aagtgcaagg tctccaacaa agccctccca  2340
gcccccatcg agaaaaccat ctccaaagcc aaagggcagc cccgagaacc acaggtgtac  2400
accctgcccc catcccggga ggagatgacc aagaaccagg tcagcctgac ctgcctggtc  2460
aaaggcttct atcccagcga catcgccgtg gagtgggaga gcaatgggca gccggagaac  2520
aactacaaga ccacgcctcc cgtgctggac tccgacggct ccttcttcct ctacagcaag  2580
ctcaccgtgg acaagagcag gtggcagcag gggaacgtct tctcatgctc cgtgatgcat  2640
gaggctctgc acaaccacta cacgcagaag agcctctccc tgtctccggg taaacgaaaa  2700
agaagatcag gttcgggtgc gccagtaaag cagacattaa actttgattt gctgaaactt  2760
gcaggtgatg tagagtcaaa tccaggtcca atggcaacag ggagccgaac ctctctgctc  2820
cttgctttcg ggctcctttg cctaccgtgg ctccaagagg gctcggcaga tatccttctg  2880
actcaatccc ctgtgattct gtcagtgtca ccaggggaaa gggtcagttt ttcatgtcgc  2940
gcatctcaaa gcattggcac taacatccac tggtaccaac aacgcacaaa cggaagtccc  3000
cgcttgctca tcaagtatgc aagcgaatca atcagcggga tcccttccag gttcagtggt  3060
agtgggagtg gtacagattt cactctctca attaacagcg tagagtccga ggacatcgcc  3120
gactattatt gccaacagaa caacaactgg cctactacat ttggtgccgg tacaaaactg  3180
gagcttaaac gcggtcagcc caaggctgcc ccctcggtca ctctgttccc gccctcctct  3240
gaggagcttc aagccaacaa ggccacactg gtgtgtctca taagtgactt ctacccggga  3300
gccgtgacag tggcctggaa ggcagatagc agccccgtca aggcgggagt ggagaccacc  3360
acaccctcca aacaaagcaa caacaagtac gcggccagca gctatctgag cctgacgcct  3420
gagcagtgga agtcccacag aagctacagc tgccaggtca cgcatgaagg gagcaccgtg  3480
gagaagacag tggcccctac agaatgttca tagtctagaa taatcaacct ctggattaca  3540
aaatttgtga aagattgact ggtattctta actatgttgc tccttttacg ctatgtggat  3600
acgctgcttt aatgcctttg tatcatgcta ttgcttcccg tatggctttc attttctcct  3660
ccttgtataa atcctggttg ctgtctcttt atgaggagtt gtggcccgtt gtcaggcaac  3720
gtggcgtggt gtgcactgtg tttgctgacg caacccccac tggttggggc attgccacca  3780
cctgtcagct cctttccggg actttcgctt tccccctccc tattgccacg gcggaactca  3840
tcgccgcctg ccttgcccgc tgctggacag gggctcggct gttgggcact gacaattccg  3900
tggtgttgtc ggggaaatca tcgtcctttc cttggctgct cgcctgtgtt gccacctgga  3960
ttctgcgcgg gacgtccttc tgctacgtcc cttcggccct caatccagcg gaccttcctt  4020
cccgcggcct gctgccggct ctgcggcctc ttccgcgtct tcgccttcgc cctcagacga  4080
gtcggatctc cctttgggcc gcctccccgc ctaagcttat cgataccgtc gagatctaac  4140
ttgtttattg cagcttataa tggttacaaa taaagcaata gcatcacaaa tttcacaaat  4200
aaagcatttt tttcactgca ttctagttgt ggtttgtcca aactcatcaa tgtatcttat  4260
catgtctgga tctcgacctc gactagagca tggctacgta gataagtagc atggcgggtt  4320
aatcattaac tacaaggaac ccctagtgat ggagttggcc actccctctc tgcgcgctcg  4380
ctcgctcact gaggccgggc gaccaaaggt cgcccgacgc ccgggctttg cccgggcggc  4440
ctcagtgagc gagcgagcgc gccagctggc gtaatagcga agaggcccgc accgatcgcc  4500
cttcccaaca gttgcgcagc ctgaatggcg aatggaattc cagacgattg agcgtcaaaa  4560
tgtaggtatt tccatgagcg tttttcctgt tgcaatggct ggcggtaata ttgttctgga  4620
tattaccagc aaggccgata gtttgagttc ttctactcag gcaagtgatg ttattactaa  4680
tcaaagaagt attgcgacaa cggttaattt gcgtgatgga cagactcttt tactcggtgg  4740
cctcactgat tataaaaaca cttctcagga ttctggcgta ccgttcctgt ctaaaatccc  4800
tttaatcggc ctcctgttta gctcccgctc tgattctaac gaggaaagca cgttatacgt  4860
gctcgtcaaa gcaaccatag tacgcgccct gtagcggcgc attaagcgcg gcgggtgtgg  4920
tggttacgcg cagcgtgacc gctacacttg ccagcgccct agcgcccgct cctttcgctt  4980
tcttcccttc ctttctcgcc acgttcgccg gctttccccg tcaagctcta aatcgggggc  5040
tccctttagg gttccgattt agtgctttac ggcacctcga ccccaaaaaa cttgattagg  5100
gtgatggttc acgtagtggg ccatcgccct gatagacggt tttcgccct ttgacgttgg  5160
```

-continued

```
agtccacgtt ctttaatagt ggactcttgt tccaaactgg aacaacactc aaccctatct  5220
cggtctattc ttttgattta taagggattt tgccgatttc ggcctattgg ttaaaaaatg  5280
agctgattta acaaaaattt aacgcgaatt ttaacaaaat attaacgttt acaatttaaa  5340
tatttgctta tacaatcttc ctgtttttgg ggcttttctg attatcaacc ggggtacata  5400
tgattgacat gctagtttta cgattaccgt tcatcgattc tcttgtttgc tccagactct  5460
caggcaatga cctgatagcc tttgtagaga cctctcaaaa atagctaccc tctccggcat  5520
gaatttatca gctagaacgg ttgaatatca tattgatggt gatttgactg tctccggcct  5580
ttctcacccg tttgaatctt tacctacaca ttactcaggc attgcattta aaatatatga  5640
gggttctaaa aatttttatc cttgcgttga aataaaggct tctcccgcaa aagtattaca  5700
gggtcataat gtttttggta caaccgattt agctttatgc tctgaggctt tattgcttaa  5760
ttttgctaat tctttgcctt gcctgtatga tttattggat gttggaattc ctgatgcggt  5820
attttctcct tacgcatctg tgcggtattt cacaccgcat atggtgcact ctcagtacaa  5880
tctgctctga tgccgcatag ttaagccagc cccgacaccc gccaacaccc gctgacgcgc  5940
cctgacgggc ttgtctgctc ccggcatccg cttacagaca agctgtgacc gtctccggga  6000
gctgcatgtg tcagaggttt tcaccgtcat caccgaaacg cgcgagacga aagggcctcg  6060
tgatacgcct atttttatag gttaatgtca tgataataat ggtttcttag acgtcaggtg  6120
gcacttttcg gggaaatgtg cgcggaaccc ctatttgttt atttttctaa atacattcaa  6180
atatgtatcc gctcatgaga caataaccct gataaatgct tcaataatat tgaaaaagga  6240
agagtatgag tattcaacat ttccgtgtcg cccttattcc cttttttgcg gcattttgcc  6300
ttcctgtttt tgctcaccca gaaacgctgg tgaaagtaaa agatgctgaa gatcagttgg  6360
gtgcacgagt gggttacatc gaactggatc tcaacagcgg taagatcctt gagagttttc  6420
gccccgaaga acgttttcca atgatgagca cttttaaagt tctgctatgt ggcgcggtat  6480
tatcccgtat tgacgccggg caagagcaac tcggtcgccg catacactat tctcagaatg  6540
acttggttga gtactcacca gtcacagaaa agcatcttac ggatggcatg acagtaagag  6600
aattatgcag tgctgccata accatgagtg ataacactgc ggccaactta cttctgacaa  6660
cgatcggagg accgaaggag ctaaccgctt ttttgcacaa catgggggat catgtaactc  6720
gccttgatcg ttgggaaccg gagctgaatg aagccatacc aaacgacgag cgtgacacca  6780
cgatgcctgt agcaatggca acaacgttgc gcaaactatt aactggcgaa ctacttactc  6840
tagcttcccg gcaacaatta atagactgga tggaggcgga taaagttgca ggaccacttc  6900
tgcgctcggc ccttccggct ggctggttta ttgctgataa atctggagcc ggtgagcgtg  6960
ggtctcgcgg tatcattgca gcactggggc cagatggtaa gccctcccgt atcgtagtta  7020
tctacacgac ggggagtcag gcaactatgg atgaacgaaa tagacagatc gctgagatag  7080
gtgcctcact gattaagcat tggtaactgt cagaccaagt ttactcatat atactttaga  7140
ttgatttaaa acttcatttt taatttaaaa ggatctaggt gaagatcctt tttgataatc  7200
tcatgaccaa aatcccttaa cgtgagtttt cgttccactg agcgtcagac cccgtagaaa  7260
agatcaaagg atcttcttga gatccttttt ttctgcgcgt aatctgctgc ttgcaaacaa  7320
aaaaaccacc gctaccagcg gtggtttgtt tgccggatca agagctacca actctttttc  7380
cgaaggtaac tggcttcagc agagcgcaga taccaaatac tgtccttcta gtgtagccgt  7440
agttaggcca ccacttcaag aactctgtag caccgcctac atacctcgct ctgctaatcc  7500
tgttaccagt ggctgctgcc agtggcgata agtcgtgtct taccgggttg gactcaagac  7560
gatagttacc ggataaggcg cagcggtcgg gctgaacggg gggttcgtgc acacagccca  7620
gcttggagcg aacgacctac accgaactga gatacctaca gcgtgagcta tgagaaagcg  7680
ccacgcttcc cgaagggaga aaggcggaca ggtatccggt aagcggcagg gtcggaacag  7740
gagagcgcac gagggagctt ccagggggaa acgcctggta tctttatagt cctgtcgggt  7800
ttcgccacct ctgacttgag cgtcgatttt tgtgatgctc gtcagggggg cggagcctat  7860
ggaaaaacgc cagcaacgcg gcctttttac ggttcctggc cttttgctgg ccttttgctc  7920
acatgttctt tcctgcgtta tcccctgatt ctgtggataa ccgtattacc gcctttgagt  7980
gagctgatac cgctcgccgc agccgaacga ccgagcgcag cgagtcagtg agcgaggaag  8040
cggaagagcg cccaatacgc aaaccgcctc tccccgcgcg ttggccgatt cattaatgca  8100
gcag                                                                8104
```